United States Patent [19]
Tanaka et al.

[11] Patent Number: 5,430,146
[45] Date of Patent: Jul. 4, 1995

[54] SPIROOXAZINE COMPOUNDS

[75] Inventors: Takashi Tanaka; Shinsuke Tanaka; Seiji Okazaki, all of Tokuyama, Japan

[73] Assignee: Tokuyama Corporation, Tokuyama, Japan

[21] Appl. No.: 218,695

[22] Filed: Mar. 28, 1994

Related U.S. Application Data

[63] Continuation of Ser. No. 895,661, Jun. 9, 1992, abandoned.

[30] Foreign Application Priority Data

Jun. 10, 1991 [JP] Japan .................. 3-138052

[51] Int. Cl.$^6$ .................. C07D 413/04; C07D 417/04
[52] U.S. Cl. ...................................... 544/71
[58] Field of Search ........................... 544/71

[56] References Cited

U.S. PATENT DOCUMENTS

| | | | |
|---|---|---|---|
| 4,637,698 | 1/1987 | Kwak et al. | 351/163 |
| 4,719,296 | 1/1988 | Irie et al. | 544/71 |
| 4,931,219 | 6/1990 | Kwiatkowski et al. | 252/586 |
| 4,986,934 | 1/1991 | Kwiatkowski et al. | 252/586 |
| 5,017,698 | 5/1991 | Machida et al. | 544/71 |
| 5,139,707 | 8/1992 | Guglielmetti et al. | 252/586 |

OTHER PUBLICATIONS

Chemical Abstracts 117(16) 152139z, Tanaka et al., abstract of JP 04 072362 A2 Mar. 6, 1992.
Chemical Abstracts 116(14) 140,182z, Imura et al., abstract of JP 03 251587 A2, Nov. 11, 1991.
Chemical Abstracts 116(13) 128,941, Murakami et al., abstract of JP 03 227989 A2, Oct. 8, 1991.
Chemical Abstracts 115(22) 244,133, Tokuyama Soda, abstract of JP 03095184 A2, Apr. 19, 1991.
Chem. Abstr. 114(14) 133,085, Murayama et al., Abstract of JP 02 225486 A2, Sep. 7, 1990.
Chem. Abstr. 109(12) 101,935, Tateoka et al., Abstract of JP 63 030487 A2 Feb. 9, 1988.
Chemical Abstract 109(10) 83544, Tateoka et al., Abstract of JP 63030486 A2, Feb. 9, 1988.

*Primary Examiner*—Mukund J. Shah
*Assistant Examiner*—Matthew V. Grumbling
*Attorney, Agent, or Firm*—Sherman and Shalloway

[57] ABSTRACT

Disclosed is a novel spirooxazine compound having excellent durability which changes into a colored form upon irradiation with the light containing ultraviolet rays such as of sunrays or the light from a mercury lamp, the change being reversible.

6 Claims, 2 Drawing Sheets

SPIROOXAZINE COMPOUNDS

This application is a continuation of application Ser. No. 07/895,661, filed Jun. 9, 1992, now abandoned.

DETAILED DESCRIPTION OF THE INVNETION

1. Field of Industrial Application

Figure 1:
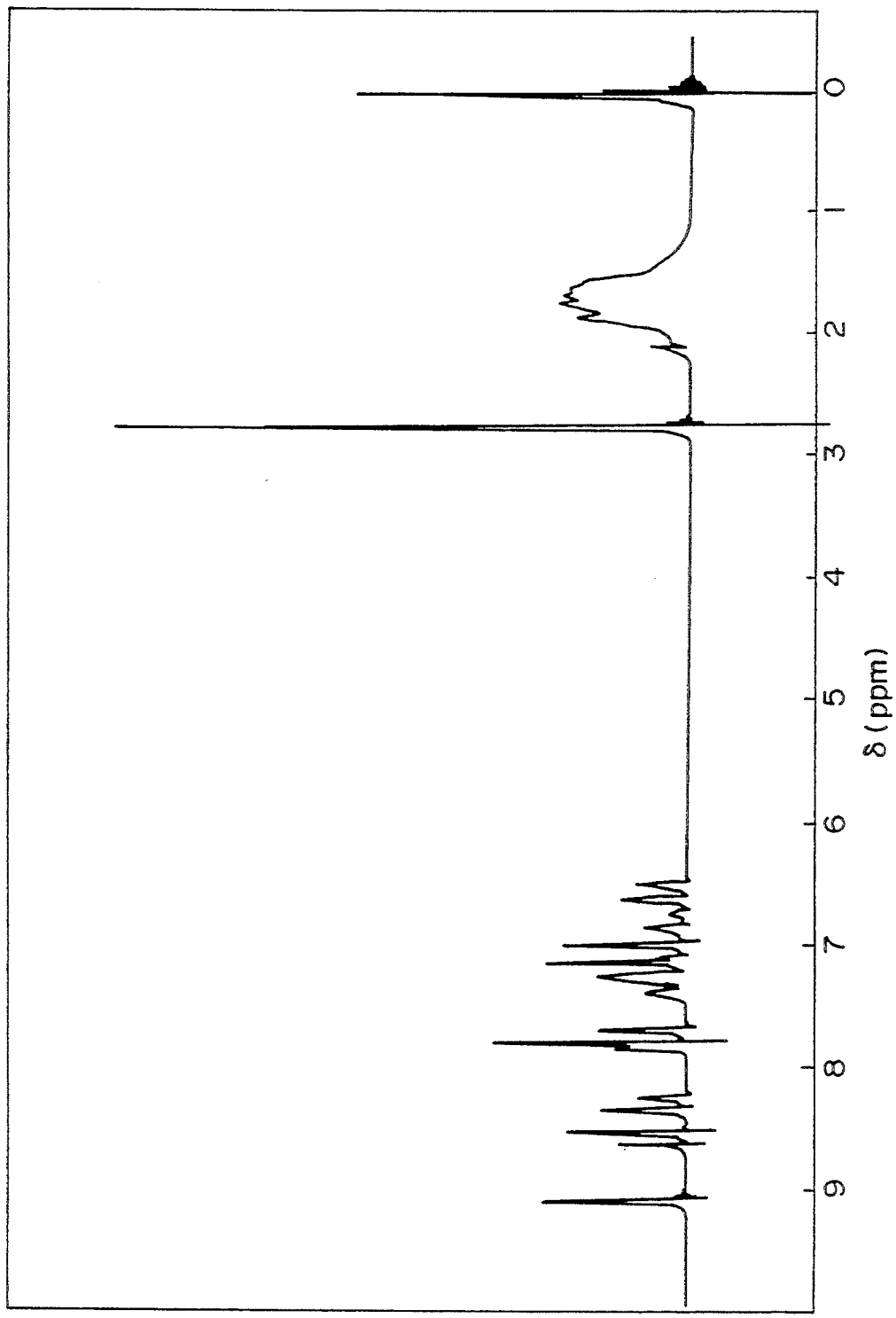

The present invention relates to a novel spirooxazine compound having excellent durability which changes into a colored form upon irradiation with the light containing ultraviolet rays such as sunrays or the light from a mercury lamp, the change being reversible.

2. Prior Art

Photochromism is a phenomenon that has drawn attention in the past several years and stands for a reversible action in which a certain compound quickly changes its color when it is irradiated with light containing ultraviolet rays such as sunrays or light from a mercury lamp and the color returns to the original color when the compound is no more irradiated with light but is left in a dark place. The compounds having such properties are called photochromic compounds and various compounds have hitherto been synthesized. Among them, spirooxazine compounds have been known to exhibit a good photochromic action in the high-molecular matrix such as in a plastic lens, but no particular commonalities has yet been recognized in the structures thereof.

PROBLEMS TO BE SOLVED BY THE INVENTION

However, none of the spirooxazine compounds that are synthesized thus far exhibit good photochromic action at around room temperature (20° to 30° C.) or at temperature higher than room temperature.

In order to solve this problem, therefore, the present invention provides a spirooxazine compound which exhibit good photochromic action at around room temperature or at temperature higher than room temperature.

MEANS FOR SOLVING THE PROBLEMS

In order to solve the above problem, the present inventors have synthesized a variety of spirooxazine compounds in order to study their photochromic actions. As a result, the inventors have arrived at and proposed the present invention.

That is, the present invention is concerned with a spirooxazine compound represented by the following formula (I)

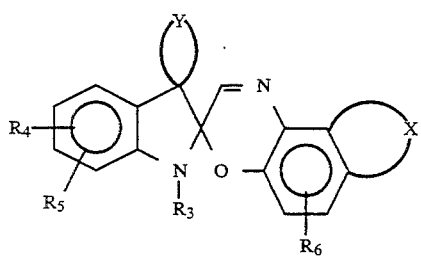

wherein

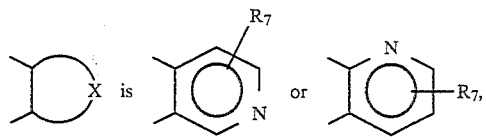

$R_7$ is a hydrogen atom, a halogen atom, an alkyl group with 1 to 10 carbon atoms, an aryl group with 6 to 10 carbon atoms, an aralkyl group with 7 to 14 carbon atoms or an alkoxy group with 1 to 10 carbon atoms,

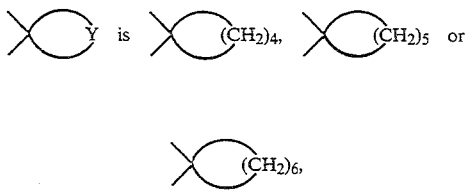

$R_3$ is an alkyl group with 1 to 10 carbon atoms, an aryl group with 6 to 10 carbon atoms, an aralkyl group with 7 to 14 carbon atoms, or an alkoxycarbonylalkyl group having an alkoxy group with 1 to 10 carbon atoms and an alkylene group with 1 to 10 carbon atoms, $R_4$ and $R_5$ are the same or different hydrogen atoms, halogen atoms, alkyl groups with 1 to 10 carbon atoms, aryl groups with 6 to 10 carbon atoms, aralkyl groups with 7 to 14 carbon atoms, alkoxy groups with 1 to 10 carbon atoms, nitro groups, cyano groups, halogenoalkyl groups with 1 to 4 carbon atoms or alkoxycarbonyl groups with 2 to 12 carbon atoms, $R_6$ is a hydrogen atom, a halogen atom, an alkyl group with 1 to 10 carbon atoms, an aryl group with 6 to 10 carbon atoms, an aralkyl group with 7 to 14 carbon atoms or an alkoxy group with 1 to 10 carbon atoms.

According to the present invention, the fact that

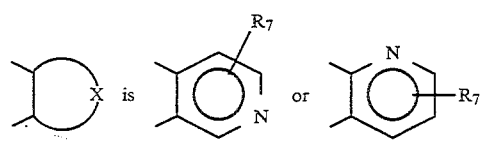

in the above general formula (I) is important to obtain a high color concentration at around room temperature or at temperatures higher than room temperature. Preferably, furthermore, a higher color concentration is obtained at around room temperature or at temperatures higher than room temperature particularly when

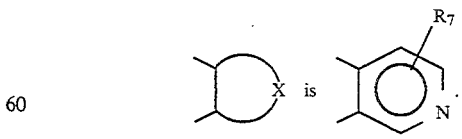

On the other hand, high color concentrations are not obtained at around room temperature or at temperature higher than room temperature by the compounds in which the positions of nitrogen atoms are other than those indicated by the above formula.

In the above general formula (I),

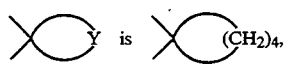 is 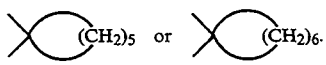

The cyclohexyl ring

is particularly preferred.

In the above general formula (I), $R_3$ is a hydrocarbon group or an alkoxycarbonylalkyl group. The hydrocarbon group may be an alkyl group with 1 to 10 or, preferably, with 1 to 4 carbon atoms, an aryl group 6 to 10 carbon atoms, or an aralkyl group with 7 to 14 carbon atoms. Among them, an alkyl group with 1 to 10 carbon atoms is preferred, and an alkyl group with 1 to 4 carbon atoms is more preferred. Concrete examples of the alkyl group include a methyl group, an ethyl group, an isopropyl group, etc. Examples of the aryl group include a phenyl group, a naphthyl group, etc. Examples of the aralkyl group include a benzyl group, a phenylethyl group, a phenylpropyl group, a naphthylmethyl group, etc.

The alkoxy group in the alkoxycarbonylalkyl denoted by $R_3$ has 1 to 10 carbon atoms and, preferably, 1 to 4 carbon atoms. The alkylene group in the alkoxycarbonylalkyl group has 1 to 10 carbon atoms, preferably, 1 to 4 carbon atoms. Concrete examples of the alkoxycarbonylalkyl group include a methoxycarbonylmethyl group, a methoxycarbonylethyl group, a methoxycarbonylpropyl group, an ethoxycarbonylmethyl group, an ethoxycarbonylethyl group, an ethoxycarbonylbutyl group, a butoxycarbonylethyl group, etc.

In the above general formula (I), $R_4$ and $R_5$ are the same or different hydrogen atoms, halogen atoms, hydrocarbon groups, alkoxy groups with 1 to 10 carbon atoms, nitro groups, cyano groups, halogenoalkyl groups with 1 to 4 carbon atoms or alkoxycarbonyl groups with 2 to 12 carbon atoms.

Examples of the halogen atom include a fluorine atom, a chlorine atom, a bromine atom and an iodine atom.

The hydrocarbon group is the one mentioned in conjunction with $R_3$.

The alkoxy group has 1 to 10 carbon atoms and, preferably, 1 to 4 carbon atoms. Concrete examples include a methoxy group, an ethoxy group, a propoxy group and a butoxy group.

The halogen atom in the halogenoalkyl group may be fluorine, chlorine or bromine, and the alkyl group has 1 to 4 carbon atoms. Concrete examples thereof include a trifluoromethyl group, a trichloromethyl group and a tribromomethyl group.

The above alkoxycarbonyl group has 2 to 12 carbon atoms. Concrete examples thereof include a methoxycarbonyl group, an ethoxycarbonyl group, a propoxycarbonyl group and a butoxycarbonyl group.

In the above general formula (I), furthermore, $R_6$ and $R_7$ are the same or different hydrogen atoms, halogen atoms, hydrocarbon groups or alkoxy groups. The above halogen atoms, hydrocarbon groups, and alkoxy groups are those atoms and groups mentioned in conjunction with $R_4$ and $R_5$ above.

Among the spirooxazine compounds of the present invention, a spirooxazine compound represented by the following formula (I-3)

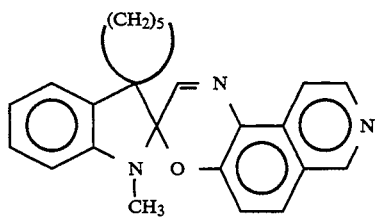

(I-3)

produces the greatest color concentration at around room temperature or at temperature higher than room temperature.

A compound in which $R_4$ and $R_5$ in the general formula (I) are the same or different fluorine atoms, fluoroalkyl groups with 1 to 4 carbon atoms or cyano groups develops a purple color and gives an advantage of being easily adjusted to a color tone of gray or brown in combination with other photochromic compounds or dyes.

The action of developing a particularly high color concentration of the spirooxazine compound represented by the general formula (I) of the present invention at high temperature compared with similar spirooxazine compounds, has not yet been clarified but can be presumed as described below.

The spirooxazine compound represented by the general formula (I) makes a great difference from the known resembling spirooxazine compounds with respect to the position at which a nitrogen atom is bonded to the pyridine ring and the presence or absence of a spiro ring consisting of hydrocarbons. The color concentration developed at high temperatures is affected by the position at which the nitrogen atom is bonded to the pyridine ring and is further greatly affected by the presence or absence of the spiro ring consisting of hydrocarbons. In the compounds of the present invention, factors that cause these effects have been specified and excellent advantage is obtained from these effects.

Described below are examples of the spirooxazine compound preferably used in the present invention.

(1) 1'-Methyldispiro(cyclohexane-1,3'-(3H) indole-2'(1'H), 3''-(3H)pyrido(4,3-f)(1,4)benzoxazine)

(2) 1'-Methyl-5'-nitrodispiro(cyclopentane-1,3,'-(3H)-indole-2'(1'H), 3''-(3H)pyrido(4,3-f)(1,4)benzoxazine)

(3) 6'-Fluoro-1'-methyldispiro(cyclohexane-1,3,'-(3H)-indole-2'(1'H), 3''-(3H)pyrido(4,3-f)(1,4)benzoxazine)

(4) 5'-Fluoro-1'-methyldispiro(cyclohexane-1,3,'-(3H)-indole-2'(1'H), 3''-(3H)pyrido(4,3-f)(1,4)benzoxazine)

(5) 4',6'-Difluoro-1'-methyldispiro(cyclohexane-1,3'-(3H)-indole-2'(1'H), 3''-(3H)pyrido(4,3-f)(1,4)benzoxazine)

(6) 1',6'-Dimethylspiro(cyclohexane-1,3,'-(3H)-indole-2'(1'H), 3''-(3H)pyrido(2,3-f)(1,4)benzoxazine)

(7) 9''-Bromo-1'-methoxycarbonylmethyl-5,'-trifluoromethyldispiro(cyclohexane-1,3,'-(3H)-indole-2'(1'H), 3''-(3H)pyrido(2,3-f)(1,4)benzoxazine)

(8) 1'-n-Butyl-6'-iododispiro(cyclohexane-1,3'-(3H)-indole-2'(1'H), 3"-(3H)pyrido(2,3-f)(1,4)-benzoxazine)

(9) 4'-Cyano-1'-(2-(methoxycarbonyl)ethyl)dispiro(cyclohexane-1,3,'-(3H)-indole-2'(1',H), 3"-(3H)pyrido(2,3-f)(1,4)benzoxazine)

(10) 1'-Methyldispiro(cyclohexane-1,3'-(3H)-indole-2'(1',H), 3"-(3H)pyrido(2,3-f)(1,4)benzoxazine)

(11) 1'-Benzyl-6'-iododispiro(cyclopentane-1,3'-(3H)-indole-2'(1', H), 3"-(3H)pyrido(2, 3-f)(1,4)benzoxazine)

(12) 1'-Methyl-5'-trichloromethyldispiro(cyclohexane-1,3'-(3H)-indole-2'(1',H), 3"-(3H)pyrido(2,3-f)(1,4)benzoxazine)

(13) 1'-Methoxycarbonylmethyldispiro(cyclohexane-1,3'-(3H)-indole-2'(1',H), 3'-(3H)pyrido(2,3-f)(1,4)benzoxazine)

The compound represented by the aforementioned general formula (I) of the present invention is a novel one which usually exists as a colorless or pale yellow solid or viscous liquid at ordinary temperature under pressure, and can be confirmed by the below-mentioned means (a) to (d).

(a) Measurement of nuclear magnetic resonance spectra ($^1$H-NMR) of protons make it possible to learn the kind and number of protons present in the molecules.

That is, spectra based on the aromatic protons and oxazine ring protons appear near $\delta 6.6$ to 9 ppm, spectra based on the protons of an alkyl group appear near $\delta 1.5$ ppm, and spectra based on the protons of carbon to which nitrogen is bonded in $R_3$ appears near $\delta 2$ to 4 ppm. By comparing the intensities of $\delta$ spectra, furthermore, it is possible to learn the number of protons of the bonding groups.

(b) Elemental analyses make it possible to find the weight ratios of carbon, hydrogen, nitrogen, sulfur and halogen. It is, further, possible to calculate weight ratio of oxygen substracting from 100 the sum of weight ratios of the elements that are perceived. It is therefore allowed to determine the composition of the corresponding product.

(c) Measurement of $^{13}$C-nuclear magnetic resonance spectra ($^{13}$C-NMR) makes it possible to learn the kind of carbon present in the molecules.

Spectra based upon primary carbon and secondary carbon appear near $\delta 20$ to 50 ppm, spectra based upon the aromatic hydrocarbon group or upon carbon of an unsaturated heterocyclic group appear near $\delta 110$ to 150 ppm, spectra based upon spirocarbon appear near $\delta 100$ ppm, and spectra based upon carbon of carbonyl appear near $\delta 170$ ppm.

(d) Measurement of infrared absorption spectrum (IR) makes it possible to learn the kind of functional group present in the molecules. As representative examples of absorption, there appear spectral absorption due to C=N bond near 1620 cm$^{-1}$, spectral absorption due to aromatic C—H bond near 1480 cm$^{-1}$ and spectral absorption due to ether bond near 1250 cm$^{-1}$.

The compound represented by the general formula (I) of the present invention can be synthesized by any method without any particular limitation. A representative method that is suitably employed will now be described.

A method of reacting a compound represented by the following general formula (II)

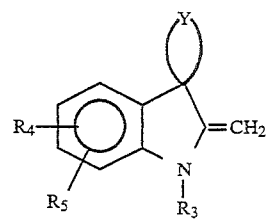

wherein

is a cycloalkyl ring with 5 to 7 carbon atoms, $R_3$ is an alkyl group with 1 to 10 carbon atoms, an aryl group with 6 to 10 carbon atoms, an aralkyl group with 7 to 14 carbon atoms or an alkoxycarbonylalkyl group having an alkoxy group with 1 to 10 carbon atoms and an alkylene group with 1 to 10 carbon atoms, and $R_4$ and $R_5$ are the same or different hydrogen atoms, halogen atoms, alkyl groups with 1 to 10 carbon atoms, aryl groups with 6 to 10 carbon atoms, aralkyl groups with 7 to 14 carbon atoms, alkoxy group with 1 to 10 carbon atoms, nitro groups, cyano groups, halogenoalkyl groups with 1 to 4 carbon atoms or alkoxycarbonyl groups with 2 to 12 carbon atoms.

with a nitroso compound represented by the general formula (III)

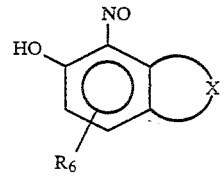

wherein

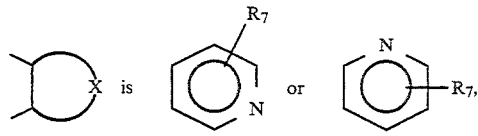

$R_6$ and $R_7$ may be the same or different hydrogen atoms, halogen atoms, an alkyl group with 1 to 10 carbon atoms, aryl groups with 6 to 10 carbon atoms, an aralkyl group with 7 to 14 carbon atoms or an alkoxy group with 1 to 10 carbon atoms.

The reaction of the compound represented by the above general formula (II) with the compound represented by the general formula (III) is carried out as described below.

The reaction ratio of these two kinds of compounds may lie over a wide range but usually lies over a range of 1:10 to 10:1 (molar ratio). The reaction temperature should usually range from 0° to 200° C., and the solvent should be such an organic solvent as methyl alcohol, ethyl alcohol, N-methylpyrrolidone, dimethylformamide, tetrahydrofuran, benzene or toluene.

The spirooxazine compound represented by the above general formula (I) of the present invention dissolves well in a general organic solvent such as toluene, chloroform or tetrahydrofurane. When the spirooxazine compound represented by the general formula (I) is dissolved in the solvent, the solution usually remains colorless and transparent and exhibits a good reversible photochromic action is which it quickly develops color when it is irradiated with sunrays or with ultraviolet rays and quickly returns to the initial colorless state when the light is interrupted.

The photochromic action of the compound of the general formula (I) takes place even in a high molecular solid matrix, and the speed of the reversion is of the order of seconds. Such a high molecular matrix may be the one in which the spirooxazine compound represented by the general formula (I) of the present invention is uniformly dispersed. Optically preferred examples include polymers such as a poly(methyl acrylate), a poly(ethyl acrylate), a poly(methyl methacrylate), a poly(ethyl methacrylate), a polystyrene, a polyacrylonitrile, a poly(vinyl alcohol), a polyacrylamide, a poly(2-hydroxyethyl methacrylate), a poly(dimethylsiloxane), a polycarbonate and a poly(allyldiglycol carbonate), or monomers that form these polymers, or polymers obtained by copolymerizing the above monomers with other monomers.

The spirooxazine compound of the present invention can be used as a photochromic material over a wide range such as a variety of memory materials, copying materials, photosensitive materials for printing, a memory material for cathode-ray tubes, photosensitive material for laser applications and photosenitive materials for holography to substitute for silver salt photosensitive materials. The photochromic material using the spirooxazine compound of the present invention can be further used as a material of photochromic lens, as a material of optical filters, as a display material, as an actinometer and as a material of ornaments. When used as a photochromic lens, for instance, there is no particular limitation provided there is obtained uniform dimming performance. Concrete examples include a method in which a polymer film having the photochromic material of the present invention uniformly dispersed therein is sandwiched in the lenses and a method in which the compound of the invention is dissolved in, for example, a silicone oil with which the lens surfaces are impregnated at 150° to 200° C. over a period of 10 to 60 minutes, and the surfaces are covered with a hardening material to obtain photochromic lenses. There can further be proposed a method in which the polymer film is applied onto the lens surfaces which are then covered with a hardening material to obtain photochromic lenses. (Effects)

The spirooxazine compound of the present invention exhibits distinguished photochromic action in the high molecular matrix not only around room temperature (20° to 30° C.) but also at temperature (30° to 40° C.) higher than room temperature. Moreover, the spirooxazine compound of the present invention is not or is only slightly colored under the condition where it is not irradiated with ultraviolet rays since coloring due to thermochromism or solvatochromism has been suppressed.

The conventional spirooxazine compound represented by the aforementioned formula (A) develops a blue color whereas the spirooxazine compound of the present invention develop a purple to bluish purple color. This makes it possible to easily adjust to gray and brown color tones by combining it with a photochromic compound of other color tone such as a compound that develops, for example, a yellow color.

EXAMPLES

The invention will be described in further detail by way of examples but it should be noted that the invention is in no way limited thereto only.

Example 1

2.13 Grams (0.01 mole) of a compound represented by the following formula

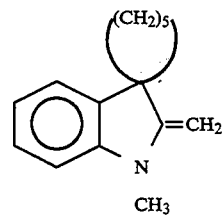

and 1.74 g (0.01 mole) of a compound represented by the following formula

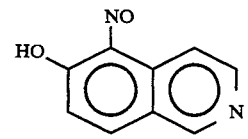

were dissolved in 100 ml of an ethyl alcohol and were refluxed for two hours. After the reaction, the solvent was removed, and 2.0 g of a spirooxazine compound of the following formula

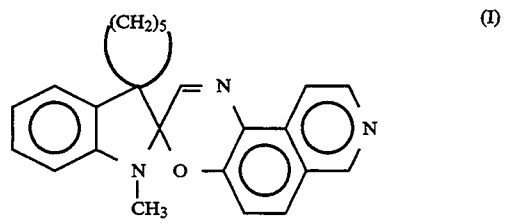

(I)

was obtained through refining by the chromatography on the silica gel.

The elemental analysis of the above compound was C 77.99%, H 6.26%, N 11.42% and O 4.33%, which was in very good agreement which C 78.02%, H 6.28%, N 11.37% and O 4.33% for $C_{24}H_{23}N_3O$.

Measurement of the nuclear magnetic resonance spectra of protons (FIG. 1) indicated spectra of 10H based on protons of a quinoline ring, protons of an indoline ring and protons of an oxazine ring near $\delta 6.58$ to 9.10 ppm, spectra of 3H based on protons of a

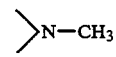

bond near $\delta 3.26$ ppm, and spectra of 10H based on protons of a cyclohexyl group near $\delta 1.20$ to 2.2 ppm.

Moreover, measurement of $^{13}C$-nuclear magnetic resonance spectra indicated spectra based on carbons of benzene ring, quinoline ring and oxazine ring of indoline near δ100 to 160 ppm, spectra based on spiro-carbon near δ99 ppm, and spectra based on carbon of a cyclohexyl group near δ20 tp 30 ppm.

Measurement of the infrared absorption spectra (IR) indicated spectral absorption due to C=N bond near 1620 cm$^{-1}$, spectral absorption due to aromatic C—H bond near 1480 cm$^{-1}$, and spectral absorption due to ether bond near 1250 cm$^{-1}$.

From the above results, it was confirmed that the isolated product was the one represented by the above structural formula (I).

Examples 2 to 13

The spirooxazine compounds shown in Table 1 were synthesized in the same manner as in Example 1.

The obtained products were analyzed for their structures by using the same manners of confirming the structure as that of Example 1, and were confirmed to be the compounds represented by the structural formulas shown in Table 1.

Table 1 further shows values of elemental analyses of the compounds, values calculated from the structural formulas of the compounds and characteristic infrared absorption spectra.

TABLE 1

| Compound No. | Spirooxazine compound | Measured C | H | N | O | others | Calculated C | H | N | O | others | Infrared absorption (cm⁻¹) |
|---|---|---|---|---|---|---|---|---|---|---|---|---|
| 2 | (CH₂)₄ structure with O₂N-phenyl and naphthoxazine, N—CH₃ | 68.94 | 5.04 | 14.02 | 12.0 | — | 68.99 | 5.03 | 13.99 | 11.99 | — | 1618, 1572, 1491, 1365, 1250, 1093, 1032, 969, 831, 755 |
| 3 | (CH₂)₅ structure with F-phenyl and naphthoxazine, N—CH₃ | 73.62 | 5.89 | 11.20 | 4.27 | F:5.02 | 73.58 | 5.91 | 11.19 | 4.26 | F:5.06 | 1619, 1492, 1461, 1256, 1243, 1093, 1037, 971, 830, 775 |
| 4 | (CH₂)₅ structure with F-phenyl and naphthoxazine, N—CH₃ | 73.51 | 6.02 | 11.14 | 4.20 | F:5.13 | 73.58 | 5.91 | 11.19 | 4.26 | F:5.06 | 1620, 1493, 1459, 1253, 1240, 1091, 1038, 970, 828, 772 |
| 5 | (CH₂)₅ structure with difluoro-phenyl and naphthoxazine, N—CH₃ | 71.08 | 5.31 | 10.31 | 4.03 | F:9.27 | 71.10 | 5.22 | 10.36 | 3.95 | F:9.37 | 1621, 1493, 1459, 1258, 1245, 1094, 1035, 968, 829, 772 |
| 6 | (CH₂)₅ structure with H₃C-phenyl and naphthoxazine, N—CH₃ | 79.29 | 5.40 | 11.09 | 4.22 | — | 79.34 | 5.33 | 11.10 | 4.23 | — | 1620, 1493, 1460, 1254, 1095, 1036, 968, 759 |

TABLE 1-continued

| Compound No. | Spirooxazine compound | Measured C | H | N | O | others | Calculated C | H | N | O | others | Infrared absorption (cm$^{-1}$) |
|---|---|---|---|---|---|---|---|---|---|---|---|---|
| 7 | ![structure with (CH$_2$)$_4$, H$_3$C, Br, CH$_2$COOCH$_3$] | 55.68 | 3.83 | 7.53 | 8.55 | Br:14.18 F:10.23 | 55.73 | 3.78 | 7.50 | 8.57 | Br:14.26 F:10.17 | 1735 1618 1487 1459 1278 1253 1096 1037 965 753 592 487 |
| 8 | ![structure with (CH$_2$)$_6$, I, (CH$_2$)$_3$CH$_3$] | 60.92 | 5.53 | 7.63 | 2.84 | I:23.08 | 60.98 | 5.48 | 7.62 | 2.90 | I:23.01 | 1618 1487 1452 1257 1096 1037 969 758 571 479 |
| 9 | ![structure with NC, (CH$_2$)$_5$, (CH$_2$)$_3$COOCH$_3$] | 72.01 | 5.68 | 12.05 | 10.26 | — | 72.09 | 5.62 | 12.01 | 10.29 | — | 2263 1729 1618 1485 1457 1282 1251 1097 1036 968 754 |
| 10 | ![structure with (CH$_2$)$_5$, CH$_3$] | 77.98 | 6.31 | 11.35 | 4.36 | — | 78.02 | 6.27 | 11.37 | 4.33 | — | 1620 1484 1453 1251 1096 1028 974 835 753 |

TABLE 1-continued
| Compound No. | Spirooxazine compound | Measured | | | | | Calculated | | | | | Infrared absorption (cm$^{-1}$) |
|---|---|---|---|---|---|---|---|---|---|---|---|---|
| | | C | H | N | O | others | C | H | N | O | others | |
| 11 | 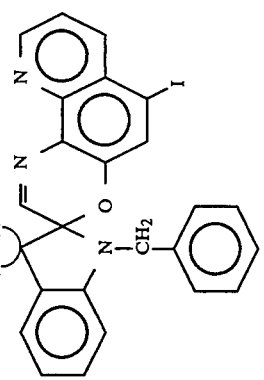 | 62.42 | 4.40 | 7.58 | 2.88 | I:22.72 | 62.49 | 4.34 | 7.54 | 2.87 | I:22.77 | 1618 1492 1460 1258 1094 1035 971 771 569 |
| 12 | 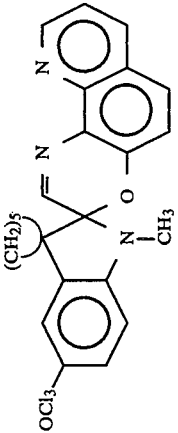 | 61.64 | 4.59 | 8.63 | 3.25 | Cl:21.89 | 61.68 | 4.55 | 8.63 | 3.29 | Cl:21.85 | 1618 1495 1458 1254 1091 1037 968 778 628 572 |
| 13 | 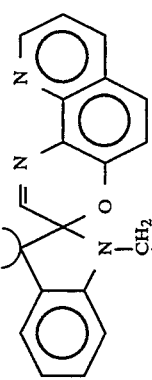 | 72.97 | 5.93 | 9.87 | 11.23 | — | 73.05 | 5.89 | 9.83 | 11.23 | — | 1739 1618 1485 1453 1278 1251 1092 1034 968 754 |

Example 14

The spirooxazine compound obtained in Example 1 was dissolved and dispersed in a poly(methyl methacrylate) using benzene and was dropped on a slide glass (11.2×3.7 cm) to prepare a cast film. The concentration of the above compound contained in the film was adjusted to be $1.0 \times 10^{-4}$ mol/g and its thickness was selected to be 0.1 mm. This photochromic film was irradiated with a mercury lamp SHL-100 manufactured by Toshiba Co. at a temperature of $35°\pm1°$ C. from a distance of 10 cm for 60 seconds to develop a color and to measure its photochromic properties. The photochromic properties were expressed as described below. The results were as shown in Table 2.

Maximum absorption wavelength ($\lambda_{max}$):
   The wavelength $\lambda_{max}$ (unit in nm) of the color-developing film was found by using a spectrophotometer 220A manufactured by Hitachi, Ltd.

$\epsilon(60)$:
   Absorbancy of the film at the maximum absorption wavelength 60 seconds after the irradiation with light under the above-mentioned condition.

$\epsilon(0)$:
   Absorbancy of the non-irradiated film under the condition of being irradiated with light at the maximum absorption wavelength.

The photochromic films were obtained in the same manner as described above with the exception of using the spirooxazine compounds obtained in Examples 2 to 13. Their properties were as shown in Table 2.

For the purpose of comparison, furthermore, Table 2 also shows the properties of a compound represented by the following formula, (Comparative Example 1)

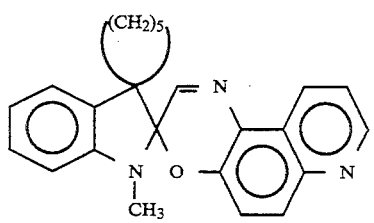

TABLE 2

| Compound No. | $\epsilon$ (0) | $\epsilon$ (60) | Developed color tone | $\lambda$ max (nm) |
|---|---|---|---|---|
| 1 | 0.089 | 1.15 | bluish purple | 599 |
| 2 | 0.072 | 0.90 | bluish purple | 595 |
| 3 | 0.082 | 0.94 | purple | 592 |
| 4 | 0.090 | 1.00 | purple | 590 |
| 5 | 0.066 | 0.90 | purple | 588 |
| 6 | 0.086 | 1.05 | bluish purple | 601 |
| 7 | 0.065 | 0.80 | purple | 585 |
| 8 | 0.070 | 0.91 | purple | 592 |
| 9 | 0.071 | 0.93 | purple | 592 |
| 10 | 0.101 | 1.05 | bluish purple | 601 |
| 11 | 0.073 | 1.00 | bluish purple | 601 |
| 12 | 0.054 | 0.90 | purple | 589 |
| 13 | 0.079 | 0.92 | purple | 592 |
| Comparative Example 1 | 0.082 | 0.65 | blue | 612 |

BRIEF DESCRIPTION OF THE DRAWINGS (FIG. 1) FIG. 1 shows nuclear magnetic resonance spectra of protons of a spirooxazine compound of Example 1.

Figure 2:
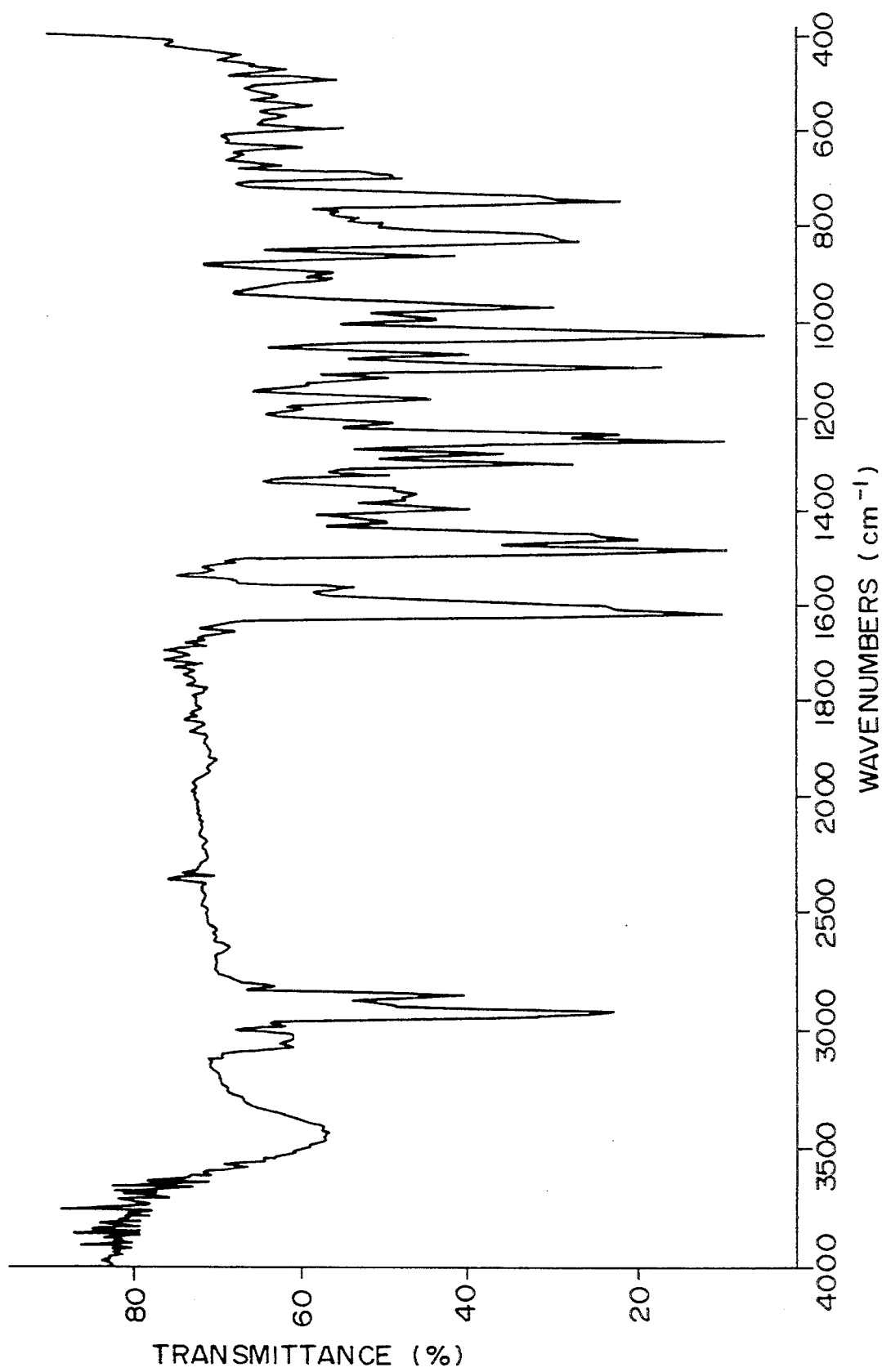

(FIG. 2) FIG. 2 shows infrared absorption spectra of the spirooxazine compound of Example 1.

We claim:

1. A spirooxazine compound represented by the following formula (I)

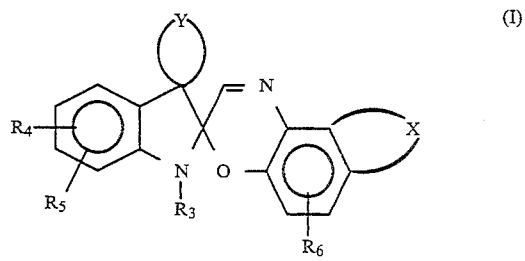

wherein

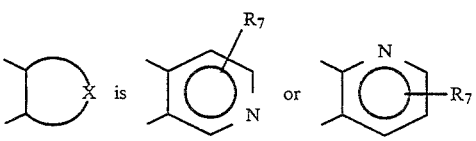

$R_7$ is a hydrogen atom or a halogen atom,

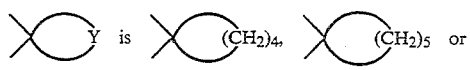

$R_3$ is an alkyl group with 1 to 10 carbon atoms, an aralkyl group with 7 to 14 carbon atoms, or an alkoxycarbonylalkyl group having an alkoxy group with 1 to 10 carbon atoms and an alkylene group with 1 to 10 carbon atoms, $R_4$ and $R_5$ which may be the same or different are selected from the group consisting of hydrogen atoms, halogen atoms, alkyl groups with 1 to 10 carbon atoms, nitro groups, cyano groups and halogenoalkyl groups with 1 to 4 carbon atoms, and $R_6$ is a hydrogen atom or a halogen.

2. A spirooxazine compound according to claim, wherein

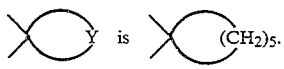

3. A spirooxazine compound represented by the following formula (I-2)

4. A spirooxazine compound according to claim 1, wherein

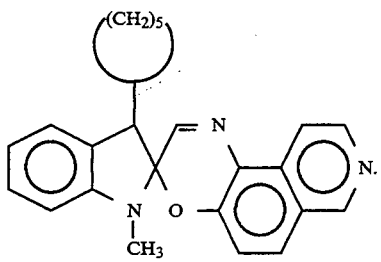

(I-2)

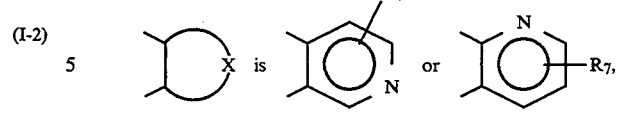

$R_7$ is a hydrogen atom or a halogen atom.

5. A spirooxazine compound according to claim 1, wherein $R_4$ and $R_5$, which may be the same or different, each represent a hydrogen atom, a halogen atom, an alkyl group with 1 to 10 carbon atoms, a nitro group, a cyano group or a halogenoalkyl group with 1 to 4 carbon atoms.

6. A spirooxazine compound according to claim 1, wherein $R_6$ is a hydrogen atom or a halogen atom.

* * * * *